(12) United States Patent
Dubielczyk et al.

(10) Patent No.: US 9,746,496 B2
(45) Date of Patent: Aug. 29, 2017

(54) SIGNAL MEASURING SYSTEM, METHOD FOR ELECTRICALLY CONDUCTING SIGNALS AND A SIGNAL CABLE

(75) Inventors: Alexander Dubielczyk, Stuttgart (DE); Marcus Schwenk, Stuttgart (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 744 days.

(21) Appl. No.: 13/634,258

(22) PCT Filed: Mar. 29, 2011

(86) PCT No.: PCT/IB2011/051328
§ 371 (c)(1),
(2), (4) Date: Sep. 12, 2012

(87) PCT Pub. No.: WO2011/121537
PCT Pub. Date: Oct. 6, 2011

(65) Prior Publication Data
US 2013/0027058 A1    Jan. 31, 2013

(30) Foreign Application Priority Data

Apr. 1, 2010    (EP) ..................... 10158940

(51) Int. Cl.
*G01R 29/26* (2006.01)
*G01R 1/18* (2006.01)
(Continued)

(52) U.S. Cl.
CPC .............. *G01R 1/18* (2013.01); *A61B 5/7203* (2013.01); *G01R 1/24* (2013.01); *A61B 5/14551* (2013.01)

(58) Field of Classification Search
CPC ....................... A61B 5/7203–5/7214
(Continued)

(56) References Cited

U.S. PATENT DOCUMENTS 2,787,784 A * 4/1957 Meryman .............. G08B 13/26
174/113 AS
4,919,114 A    4/1990 Miyazaki
(Continued)

FOREIGN PATENT DOCUMENTS

DE    3431994 A1    4/1985
EP    0739602 A1    10/1996
(Continued)

OTHER PUBLICATIONS

Hsueh, T., et al.; A3X3.8 Gb/s Four-Wire High Speed I/O Link Based on CDMA-Like Crosstalk Cancellation; 2010; IEEE Journal of Solid-State Circuits; 45(8)1522-1532.
(Continued)

*Primary Examiner* — Patrick Assouad
*Assistant Examiner* — Demetrius Pretlow

(57) ABSTRACT

The present invention relates to a signal measurement system (100, 200, 300) for measuring a signal, the system comprising a signal detection unit (41) for detecting a raw signal, a signal processing unit (42) and a signal cable (10) electrically connecting the signal detection unit (41) with the signal processing unit (42). The signal cable (10) comprises a signal conductor (1, 2) for electrically conducting a first signal from the signal detection unit (41) to the signal processing unit (42), which first signal comprises at least the raw signal, a reference conductor (11, 12) for detecting and electrically conducting to the signal processing unit (42) only a noise signal induced by a movement of the signal cable (10) or by electromagnetic interference. In this way the effect of noise on the signal quality is reduced caused by movement of the signal cable (10) or other sources of noise that induce a noise signal in the signal cable (10), such as electromagnetic interference, while at the same time not increasing the power usage or power loss.

20 Claims, 2 Drawing Sheets

(51) Int. Cl.
*A61B 5/00* (2006.01)
*G01R 1/24* (2006.01)
*A61B 5/1455* (2006.01)

(58) Field of Classification Search
USPC .................................................. 324/613–614
See application file for complete search history.

(56) References Cited

U.S. PATENT DOCUMENTS

| | | | |
|---|---|---|---|
| 4,945,189 A | | 7/1990 | Palmer |
| 5,569,158 A | | 10/1996 | Suzuki et al. |
| 5,704,365 A | * | 1/1998 | Albrecht ............... A61B 5/0408 128/901 |
| 5,916,191 A | * | 6/1999 | Plunkett ............... A61M 1/1037 422/45 |
| 5,995,859 A | * | 11/1999 | Takahashi .......... A61B 5/14551 600/323 |
| 6,225,563 B1 | | 5/2001 | Poulsen |
| 6,506,153 B1 | * | 1/2003 | Littek et al. .................. 600/301 |
| 6,967,584 B2 | * | 11/2005 | Maki ..................... G08B 13/124 324/525 |
| 8,076,580 B2 | * | 12/2011 | Kolasa ................... H01B 11/00 174/105 R |
| 8,478,538 B2 | * | 7/2013 | McGonigle et al. ............ 702/19 |
| 2002/0129968 A1 | * | 9/2002 | Flick ....................... H01B 7/361 174/113 R |
| 2003/0178215 A1 | * | 9/2003 | Chu et al. ................... 174/35 C |
| 2003/0212312 A1 | * | 11/2003 | Coffin et al. .................. 600/300 |
| 2004/0225210 A1 | * | 11/2004 | Brosovich ............ A61B 5/0428 600/372 |
| 2005/0277826 A1 | | 12/2005 | Dunseath, Jr. |
| 2006/0178030 A1 | * | 8/2006 | Lund .................... A61B 5/0205 439/287 |
| 2006/0185886 A1 | | 8/2006 | Victor |
| 2007/0252606 A1 | | 11/2007 | Root et al. |
| 2008/0057761 A1 | | 3/2008 | Mason |
| 2008/0105449 A1 | * | 5/2008 | Kenny et al. ................... 174/34 |
| 2008/0255435 A1 | * | 10/2008 | Al-Ali et al. ................. 600/323 |
| 2008/0258755 A1 | * | 10/2008 | Cases ...................... H04B 3/32 326/22 |
| 2009/0212205 A1 | * | 8/2009 | Thomson et al. ............ 250/282 |
| 2009/0259438 A1 | * | 10/2009 | Bonner ................ G06K 9/0051 702/191 |
| 2010/0084157 A1 | * | 4/2010 | Wang ............................ 174/107 |
| 2010/0274099 A1 | * | 10/2010 | Telfort et al. ................. 600/300 |

FOREIGN PATENT DOCUMENTS

| | | |
|---|---|---|
| EP | 1273922 A1 | 1/2003 |
| WO | 2009041723 A1 | 4/2009 |

OTHER PUBLICATIONS

Jagannathan, S., et al.; Common-Mode Data Transmission Using the Binder Sheath in Digital Subscriber Lines; 2009; IEEE Trans. on Communications; 57(3)831-840.

Oeltermann, A., et al.; Simultaneous recording of neuronal signals and functional NMR imaging; 2007; Magnetic Resonance Imaging; 25:760-774.

Shen, H., et al.; The Dual-Measurement Procedure for Eliminating Systematic Interference; 1984; IEEE Trans. on Electromagnetic Compatibility; EMC-26(1)14-18.

The Measurement of EMG; Twente Medical Systems International/Applications/downloaded Sep. 6, 2012. http://www.tmsi.com/applications/the measurement of EMG.

* cited by examiner

SIGNAL MEASURING SYSTEM, METHOD FOR ELECTRICALLY CONDUCTING SIGNALS AND A SIGNAL CABLE

FIELD OF THE INVENTION

The invention relates to a signal measuring system, method for electrically conducting signals and a signal cable.

BACKGROUND OF THE INVENTION

Signal cables are used to transport signals from a source, such as a detector, sensor or microphone, to a load, such as a signal processing unit or a pre-amplifier. The signal cable must be able to transfer the signal without adding any disturbance or noise to the signal, because the disturbance or noise could change the amplitude, frequency or any other characteristic of the signal. In other words, the signal and its characteristics that are input at one end of the signal cable should be the same as the signal and its characteristics that are output at the opposite end of the signal cable.

One of the sources of noise that may be added to the signal during transport of the signal in the signal cable is tribo-electricity. The tribo-electric effect is an electrical phenomenon in which certain materials can become electrically charged by friction or being rubbed against another material. Movement of a signal cable, for example due to handling of the signal cable or due to movement of the source or load to which the signal cable is connected, leads to mechanical stress of the signal cable, such as bending, compression or stretching, which influences the internal geometry of the signal cable. This may lead to the tribo-electric effect in the signal cable in which electric charge is created which causes an additional, unwanted signal onto the raw signal and can have a significant impact on the signal to noise ratio of the raw signal.

Another source of noise is the change of the value of the coupling capacity between individual wires in the cable, between wires and shielding or between wires and surrounding environment of the cable. The changed value of the capacity can lead to electric charge, thus adding noise to the raw signal. Another source of noise is the change of electrical resistance of wires or shielding induced by cable movement. Also the change of the permeability or susceptibility of the insulator material induced by motion or acceleration can add noise to the raw signal. Furthermore, movement of the cable can change its position with respect to the surrounding environment and in this way change the permeability or susceptibility, again adding noise to the raw signal. Next to noise generated by a movement of the cable, also other sources can affect the signal in the signal cable by introducing additional noise, such as for example electromagnetical interference.

For example when physiological signals of patients are monitored, it is important to get the raw physiological signal at the patient monitor output. Any movement of the signal cables used in this patient monitoring induces a noise signal that is mixed with or added to the raw physiological signal in the signal cable, and affects the signal to noise ratio of the raw physiological signal. Especially in the case of mobile patients, wearing a physiological signal detection unit such as a pulse oximeter for measuring the oxygen saturation of the blood, the signal cable is subjected to movements, like bending, stretching, thereby inducing tribo-electric and other effects in the signal cable that is attached to the signal detection unit and thus adding noise to the raw signal. For the surveillance of these non stationary patients, small and mobile monitoring systems, for example pulse oximeter devices, are operated by small and lightweight batteries which require a low power usage to increase the lifetime of the batteries.

US 2007/0252606 A1 discloses a tri-axial cable used in semiconductor test equipment. The tri-axial cable includes a center signal conductor on which testing signals are carried from test equipment to a shielded probe. The central signal conductor is surrounded by a first dielectric layer, which is surrounded by an electrically conductive coating or dispersion layer. The conductor coating or dispersion layer is sandwiched between the first dielectric layer and an electrically conducting guard layer to reduce tribo-electric effects. In a testing operation, the guard layer is driven at the same potential as the center signal conductor such that the capacitance between the guard layer and the center layer conductor is eliminated. Accordingly, the parasitic capacitance is eliminated. This cable design reduces tribo-electric effects in an active way, thus increasing the power consumption of the cable.

SUMMARY OF THE INVENTION

It is an object of the present invention to reduce the effect of noise on the signal quality caused by movement of a signal cable or other sources of noise that induce a noise signal in the signal cable, such as electromagnetic interference, while at the same time not increasing the power usage or power loss. This object is achieved by the signal measurement system according to the invention, in which the system comprises:
  a signal detection unit for detecting a raw signal,
  a signal processing unit,
  a signal cable electrically connecting the signal detection unit with the signal processing unit, the signal cable comprising:
    a signal conductor for electrically conducting a first signal from the signal detection unit to the signal processing unit, which first signal comprises at least the raw signal; and
    a reference conductor for detecting and electrically conducting to the signal processing unit only a noise signal induced by a movement of the signal cable or by electromagnetic interference.

The signal cable conducts electrical signals, like for example electrical current signals, and transports these signals from one end of the cable to an opposite end of the cable. The signal cable is at one end connected to a signal source, i.e. the signal detection unit, and at the opposite end the signal cable is connected to a signal load, i.e. the signal processing unit. The first signal that is conducted by the signal conductor comprises at least the raw signal which is detected or measured by the signal detection unit and which is used for further signal processing and signal analysis. Ideally, the first signal should not be contaminated with noise and thus carry only the raw signal. However, in reality the first signal in most cases also comprises, in addition to the raw signal, a noise signal caused by, for example, movement of the cable or electromagnetic interference. The reference conductor according to the invention provides for a simple measurement of the noise signal caused by sources of noise such as movement of the signal cable or by electromagnetic interference to the reference conductor. In this way it is possible to compensate for the noise signal thereby improving the signal to noise ratio without increasing the power consumption, for example by increasing the current level which would be an alternative way to improve the signal to noise ratio. A reduction of the required electrical power can extend the operating time of a battery that powers the measurement system. Thereby, the battery can be less often replaced or charged, which can make the measuring system more practical, more ecologically friendly and increases its usability as a mobile device. Movement of the cable introduces, amongst others, a tribo-electric effect in the cable which contributes to the noise signal. The noise signal is thus separately available via the reference conductor for further processing of the signals by the signal processing unit. The reference conductor is able to detect movement of the signal cable, because a noise signal is generated in the reference conductor in case the cable moves, for example bends or stretches, induced by, for example, the tribo-electric effect. The reference conductor also picks up other sources of noise that are also picked up by the signal conductor, such as for example electromagnetic interference.

Preferably, the measuring system, in particular the signal detection unit, is battery powered. The signal detection unit can for example be selected from the group consisting of pulse oximeter, none invasive blood pressure detector (NIBP), temperature sensor, electroencephalograph (EEG), respiration rate detector, uterine contraction detector, fetal ultrasound detector and electrocardiograph (ECG). Preferably, the signal detection unit is a pulse oximeter.

In a preferred embodiment the signal processing unit is adapted to extract the raw signal from the first signal conducted by the signal conductor and the noise signal conducted by the reference conductor. The movement of the cable not only introduces a noise signal in the reference conductor, but will also introduce a noise signal in the signal conductor. The first signal of the signal conductor thus comprises a combined signal which includes the raw signal and the noise signal. The combined raw and noise signal is delivered to the signal processing unit via the signal conductor and the noise signal is delivered separately to the signal processing unit via the reference conductor. These inputs enable the signal processing unit to extract the raw signal. For example, the compensation for the noise signal is performed by an analog control circuit.

In a preferred embodiment the raw signal is a physiological signal of a patient. In this embodiment the signal measurement system is a patient monitoring system that monitors a physiological signal that is measured on a patient with, for example, a sensor. Everyone who is monitored by any reason, for example an athlete, a healthy person, an elderly person, is in particular also understood as a patient. Examples for a physiological signal are pulse, blood oxygen saturation, blood pressure, temperature, electrical activity of the neurons (EEG), respiration rate, uterine contractions (Toco), fetal ultrasound and/or electrical activity of the myocardial muscle (ECG).

In a preferred embodiment the electrical and geometrical properties of the reference conductor are similar to the electrical and geometrical properties of the signal conductor. In this embodiment the electrical and geometrical properties of the signal conductor and the reference conductor are similar in such a way that the noise signal induced by cable movement will be similar in both conductors. The differences between the characterizing electrical and geometrical properties of the signal and reference conductor should be negligible to get noise signals in both conductors that show a good similarity and that have negligible differences. The electrical and geometrical properties of the conductors can be characterized by, for example, the dimensions of the conductor itself, the material of the conductors, the dimensions and material of any shielding. Preferably, inspection of the cross-section of the signal cable should not reveal which conductor is the signal conductor and which conductor is the reference conductor. Also the materials used for both conductors should be the same. In other words, the electrical and geometrical properties of both conductors should show such a similarity that the noise signal, induced by cable movement, of the reference conductor reflects the noise signal induced by the cable movement in the signal conductor. In a further preferred embodiment the signal conductor comprises a first and a second signal wire surrounded by a first shielding and the reference conductor comprises a first and a second reference wire surrounded by a second shielding and at one end of the reference conductor the first reference wire is connected to the second reference wire via a terminator. This embodiment provides for a two-wire signal transport in which the reference conductor has a similar construction as the signal conductor with similar electrical and geometrical properties such that the noise signal generated by cable movement is the same in both conductors. The terminator could be a high or low impedance device, such as for example a resistor, an electrical short cut or open clamp. The choice of the type of terminator depends on the effect that should be compensated. For compensating mainly tribo-electrical noise a high impedance device is used as a terminator. In that case the reference leads work like a capacitor that is charged by the tribo-electrical noise.

In a preferred embodiment the signal measurement system further comprises a controller unit for controlling a measurement of the raw signal based on the noise signal of the reference conductor. In this way a feedback loop is provided in which the noise signal, which is available via the reference conductor, is an input for the controller unit of the signal detection unit which measures the raw signal.

Preferably, the controller unit is configured to deactivate or to activate the measuring signal detection unit based on the noise signal, for example by comparing the noise signal with a selected threshold. In particular, the controller unit can be configured to switch on one or more electronic parts of the signal detection unit, for example a lamp and/or processor, one or more complete signal detection units, or one or more circuit components, if the measurement of the raw signal is activated and/or to switch off or switch to stand-by-mode one or more electronic parts of the signal detection unit, for example a lamp and/or processor, one or more complete signal detection units, or one or more circuit components, if the measurement of the raw signal is deactivated. The controller unit can for example be a superordinate unit, such as a central monitoring unit. For example the controller unit can activate or rather deactivate the signal detection unit by connecting or interrupting the electrical power supply of the signal detection unit.

The object is also achieved by a method for electrically conducting signals via a signal cable comprising a signal conductor and a reference conductor the method comprising the steps of:
  electrically conducting via the signal conductor a first signal comprising at least a raw signal; and
  detecting and electrically conducting via the reference conductor a noise signal induced by a movement of the signal cable or by electromagnetic interference.

In a preferred embodiment of the method according to the invention the method further comprises the step of extracting the raw signal from the first signal by subtracting the noise signal detected by the reference conductor from the first signal. The movement of the cable not only introduces a noise signal in the reference conductor, but will also introduce a noise signal in the signal conductor. The first signal of the signal conductor thus comprises a combined signal which includes the raw signal and the noise signal. By subtracting, by using known signal processing techniques, the noise signal, which is separately available via the reference conductor, from the first signal, which is a combination of the raw signal and the noise signal, the raw signal is extracted.

In a preferred embodiment of the method according to the invention the method further comprises the step of controlling a measurement of the raw signal based on the noise signal. In this way a feedback loop is provided in which the noise signal, which is available via the reference conductor, is an input parameter for the control of the measurement process of the raw signal, which is, for example a sensor. In a preferred embodiment the step of controlling comprises a step of initiating the measurement of the raw signal if the detected noise signal is below a selected threshold. In this way the measurement of the raw signal only is performed if there is hardly any movement of the cable and, thus, the noise signal is low, resulting in a reduction of the disturbance of the first signal by a noise signal. This increases the accuracy of the measurement of the raw signal. In another preferred embodiment the step of controlling comprises a step of shutting down an ongoing measurement of the raw signal, if the detected noise signal is above or equal to a selected threshold. In this way the measurement of the raw signal is not performed if there is, for example, a non-negligible movement of the cable and, thus, the noise signal is relatively high, which would result in an increase of the disturbance of the first signal by a noise signal.

The object is also achieved by a signal cable for electrically conducting signals in which the signal cable comprises:

a signal conductor for electrically conducting a first signal comprising a raw signal; and a reference conductor for detecting and electrically conducting only a noise signal induced by a movement of the signal cable or by electromagnetic interference.

The reference conductor according to the invention provides for a simple measurement of the noise signal induced by, for example, a tribo-electric effect caused by a movement of the signal cable without adding any voltage or current signal to the reference conductor, thereby not increasing the power consumption in the signal cable. The noise signal is thus separately available for any further processing of the signals via the reference conductor. The reference conductor is able to detect movement of the signal cable, because a noise signal is generated in the reference conductor in case the cable moves, for example bends or stretches, induced by, for example, a tribo-electric effect or by electromagnetic interference.

The signal cable is used to conduct electrical signals, like voltage or current signals, and to transport these signals from one end of the cable to an opposite end of the cable. For example, the signal cable is at one end connected to a signal source, such as a sensor for detecting a raw signal, and at the opposite the signal cable is connected to a device for processing the measured signals.

In a preferred embodiment of the signal cable the electrical and geometrical properties of the reference conductor are similar to the electrical and geometrical properties of the signal conductor.

In a preferred embodiment of the signal cable the signal conductor comprises a first and a second signal wire surrounded by a first shielding and wherein the reference conductor comprises a first and a second reference wire surrounded by a second shielding and wherein at one end of the reference conductor the first reference wire is connected to the second reference wire via a terminator.

In a preferred embodiment of the signal cable the reference conductor also conducts a second signal. In this way no extra conductor is required and use is made of a conductor which is already used for another purpose, for example for conducting a control signal.

BRIEF DESCRIPTION OF THE DRAWINGS

These and other aspects of the invention will be apparent from and elucidated with reference to the embodiment(s) described hereinafter. In the following drawings.

DETAILED DESCRIPTION OF EMBODIMENTS

Figure 1:
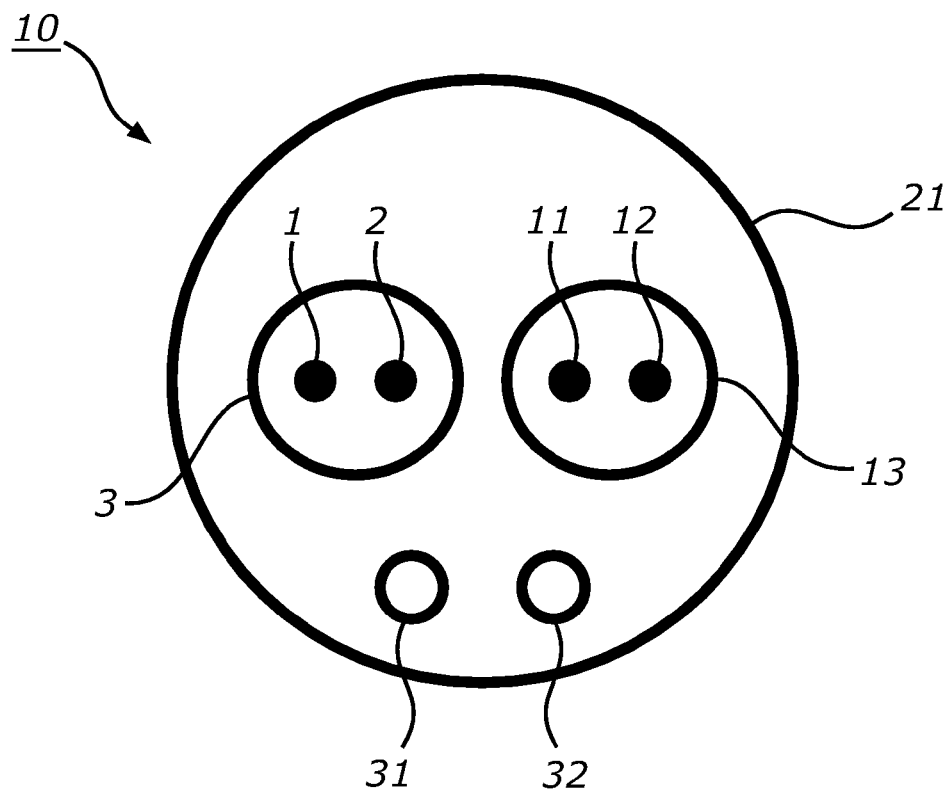
FIG. 1 is a schematic cross-section of an embodiment of a signal cable according to the invention.

FIG. 1 shows a schematic cross-section of a signal cable 10 according to the invention. The signal cable 10 comprises, in this embodiment, a first signal lead 1 and a second signal lead 2 surrounded by a first shielding 3. The first signal lead 1 and the second signal lead 2 are adapted to electrically conduct a first signal and, in combination with the first shielding 3, form a signal conductor. The first signal may be any electrical signal, such as a voltage signal or a current signal that varies in amplitude as a function of time. For example, the first signal comprises a raw signal that is measured by a sensor and that has to be transported from the sensor to a signal processing unit via the signal cable 10. The signal cable 10 further comprises a first reference lead 11 and a second reference lead 12 surrounded by a second shielding 13. The combination of the first reference lead 11, the second reference lead 12 and the second shielding 13 forms a reference conductor. The reference conductor is a copy of the signal conductor, i.e. the first and second reference leads have the same dimensions and comprise the same material as the first and second signal leads 1,2 such that the electrical and geometrical, or dimensional, properties of the reference conductor and the signal conductor exhibit negligable differences. This means that also the first shielding 3 and the second shielding 13 should have similar electrical and geometrical properties and that the relative location of the leads with respect to each other and with respect to the shielding should exhibit minimal differences. The signal cable further comprises a third shielding 21 which surrounds the signal conductor and the reference conductor. In this embodiment, the signal cable 10 also comprises a third signal lead 31 and a fourth signal lead 32, which are used to transport a second signal. This second signal is, for example, a signal that controls the measurement of the raw signal. For example, in a pulse oximeter the third and fourth signal leads 31, 32 carry the signals that control lighting devices.

The reference conductor preferably only detects and conducts a noise signal that is generated because of a tribo-electric effect in case the signal cable 10 moves, for example if the signal cable 10 bends, stretches or compresses. The reference conductor can also pick up and thus conduct other sources of noise, such as electromagnetic interference. The reference conductor preferably does not transport any other signal than the noise signal. The noise signal will also be present in and conducted by the signal cable 10 in addition to the raw signal. For example, the movement of the signal cable 10 will also induce a noise signal in the first and second signal leads 1, 2 of the signal conductor. Because of the minimal differences of the properties between the reference conductor and the signal conductor, the induced noise in the reference conductor and the signal conductor will also show minimal differences. The signal conductor then transports a combination of the raw signal and the noise signal, whereas the reference conductor only carries the noise signal. The reference conductor thus acts as a reference of the noise generated by the movement of the signal cable 10. The reference conductor does not increase the power usage of the signal conductor, because there is no active compensation technique applied to reduce the noise induces by the cable movement, instead a passive way is employed in which the reference conductor is able to detect different sources of noise, for example any movement of the signal cable 10 by only conducting the noise signal that is generated because of the tribo-electric effect.

Figure 2:
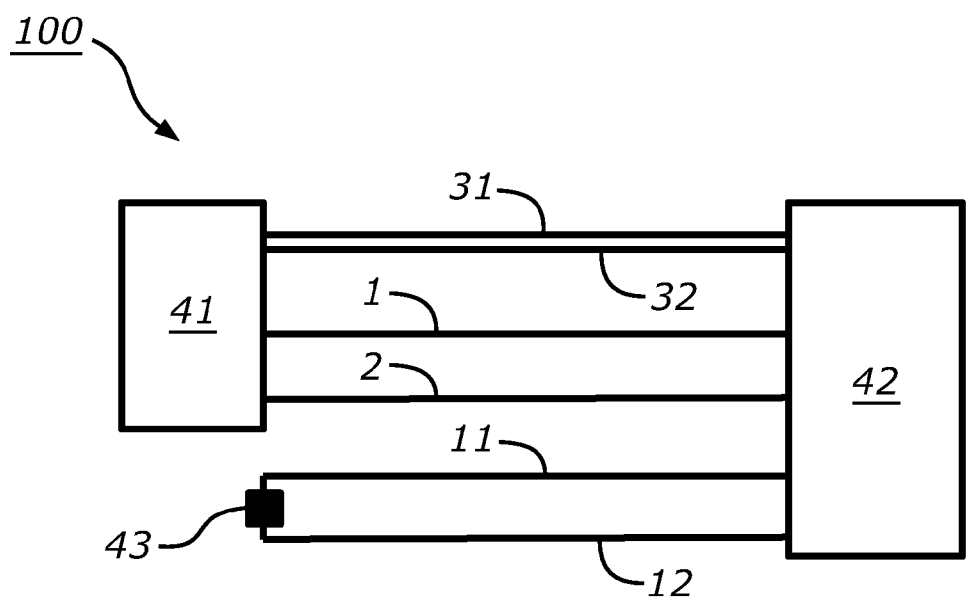
FIG. 2 is a schematic representation of an embodiment of a signal measurement system according to the invention.

FIG. 2 is a schematic representation of an embodiment of a signal measurement system 100 according to the invention. The signal measurement system 100 comprises a signal detection unit 41 which measures a raw signal. This raw signal is transported via the first and second signal leads 1, 2 of the signal conductor to a signal processing unit 42. For example, the signal detection unit 41 is a sensor that detects a physiological signal of a patient, such as a photodiode of a pulse oximeter, and the signal processing unit processes the signal received from the signal conductor and, in the example of the pulse oximeter, calculates the blood oxygen saturation from the signal received from the signal conductor. In the example of the pulse oximeter the third and fourth signal leads 31, 32 are used to transport a signal to the signal detector that controls the lighting of the pulse oximeter. The reference leads 11, 12 of the reference conductor are at one side connected to the signal processing unit 42 and are connected at the opposite side to a terminator 43. The shielding that was shown in FIG. 1 is not shown in FIG. 2 for clarity, but it should be understood that the first, second and third shielding 3, 13, 21 are also present in this embodiment. The noise signal that is for example induced by movement of the signal cable 10 is in this way transported by the reference conductor to the signal processing unit 42. The signal processing unit 42 thus has the noise signal available for further processing. For example, the signal processing unit uses the noise signal received from the first and second reference leads 11, 12 of the reference conductor to extract the raw signal from the first signal that is received from the signal conductor. In the example of the pulse oximeter, the blood oxygen saturation can then be calculated again from the raw signal in which the result is influenced to a minimal extent by noise generated by for example the tribo-electric effect or electromagnetic interference.

Figure 3:
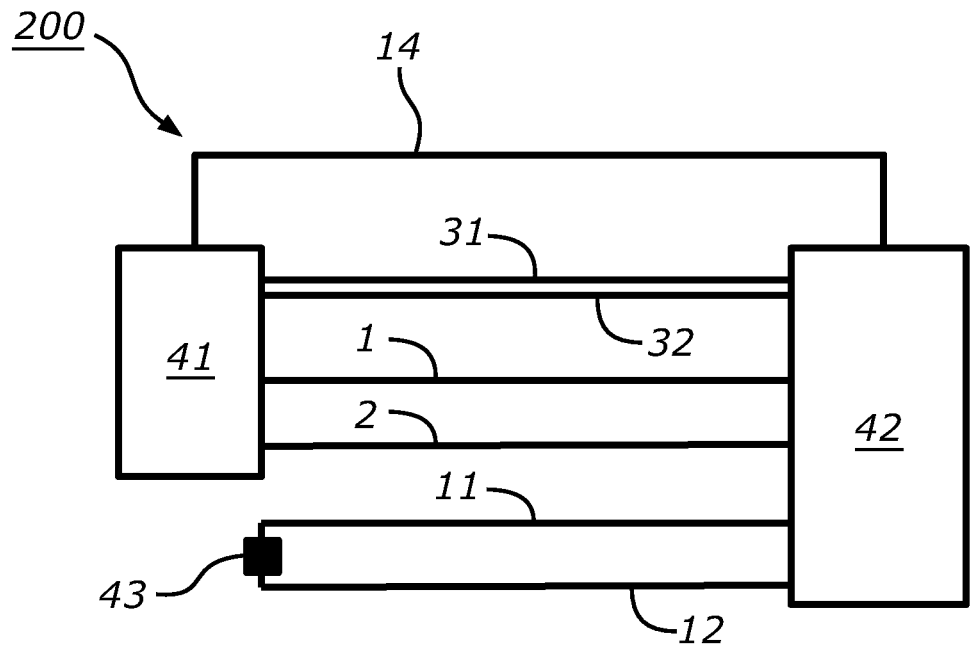
FIG. 3 is a schematic representation of another embodiment of a signal measurement system according to the invention.

FIG. 3 is a schematic representation of an embodiment of a signal measurement system 200 according to the invention. The signal measurement system 200 only differs from the signal measurement system 100 of FIG. 2 in that it comprises a feedback loop 14 in which the noise signal is used to control the measurement of the raw signal. For that purpose the signal detection unit also comprises a control unit (not shown) which receives the noise signal and which controls the measurement of the raw signal based on the noise signal. Alternatively the signal processing unit comprises the control unit (not shown). Control of the measurement based on the noise signal generated in the signal cable 10 can be advantageously used to initiate or stop the measurements and in this way control the amount of noise that has to be processed or compensated for in the signal processing unit 42. For example, if there is hardly any cable movement, then the measurement of the raw signal can be started without any significant noise induced in the signal cable 10. In another example, if the measurement is running and, after some time, the signal cable starts moving, the measurement is aborted or stopped by the control unit and the feedback loop 14 to avoid that too much noise is added to the raw signal in the signal conductor.

In general, it is preferred that the reference conductor carries the noise signal only, and no other signal, but it is also possible in an embodiment that the reference conductor may have already another primary purpose, such as coding resistors or control leads.

Figure 4:
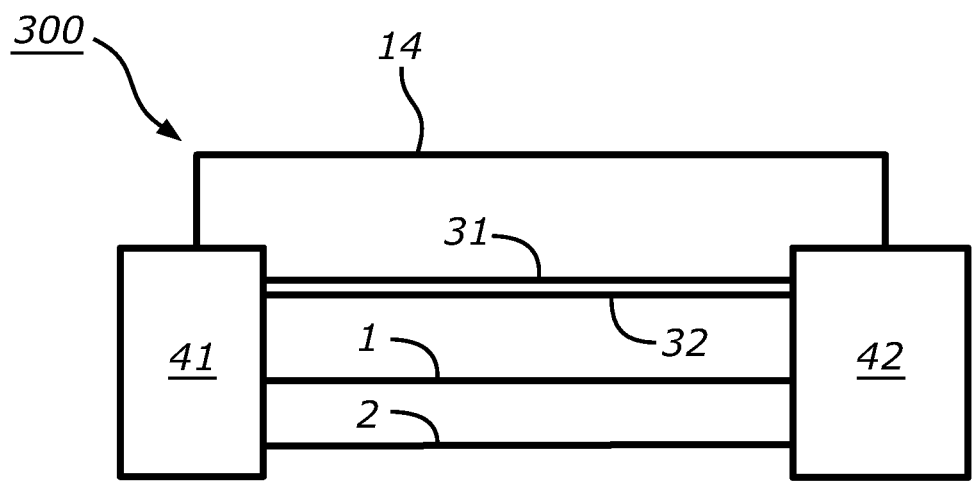
FIG. 4 is a schematic representation of another embodiment of a signal measurement system according to the invention.

FIG. 4 is a schematic representation of an embodiment of a signal measurement system 300 according to the invention. The signal measurement system 300 only differs from the signal measurement system 200 of FIG. 3 in that it does not comprise the separate reference leads 11, 12. In this embodiment the third and fourth leads 31, 32 are used as reference leads. In this case the signal processing unit 42 should apply different processing techniques to extract the raw signal from the first signal, because the third and fourth leads 31, 32 now not only carry the noise signal, but also another signal. In the example of the pulse oximeter, the third and fourth leads 31, 32 are used to conduct the control signal for the lighting to the signal detection device 41.

While the invention has been illustrated and described in detail in the drawings and foregoing description, such illustration and description are to be considered illustrative or exemplary and not restrictive; the invention is not limited to the disclosed embodiments. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. The mere fact that certain measures are recited in mutually different dependent claims does not indicate that a combination of these measures cannot be used to advantage. In the claims, the word "comprising" does not exclude other elements or steps, and the indefinite article "a" or "an" does not exclude a plurality. Any reference signs in the claims should not be construed as limiting the scope.

The invention claimed is:

1. A signal measurement system for measuring a signal, the system comprising:
   a signal detector for detecting a raw signal,
   a signal processor,
   a signal cable electrically connecting the signal detector with the signal processor, the signal cable comprising:
       a signal conductor for electrically conducting a first signal from the signal detector to the signal processor, wherein the first signal comprises at least the raw signal; and
       a reference conductor for detecting and electrically conducting a noise signal induced by a movement of the signal cable or by electromagnetic interference, and for conducting a control signal; and wherein:
the noise signal is electrically conducted to the signal processor;
first and second ends of the reference conductor are connected to the signal processor; and
the reference conductor is not connected to the signal detector.

2. The signal measurement system as claimed in claim 1, wherein the signal processor configured to extract the raw signal from the first signal conducted by the signal conductor and the noise signal conducted by the reference conductor.

3. The signal measurement system as claimed in claim 1, wherein the raw signal is a physiological signal of a patient.

4. The signal measurement system as claimed in claim 1, wherein the electrical and geometrical properties of the reference conductor are similar to the electrical and geometrical properties of the signal conductor.

5. A medical measurement system for measuring physiological information of a patient,
a medical sensor configured to sense physiological properties of the patient and generate a physiological signal;
a signal processor configured to process the physiological signal;
a cable electrically connecting the medical sensor and the signal processor, the cable including:
a signal conductor including a first and a second signal wire surrounded by a first shielding,
a reference conductor including a first and a second reference wire surrounded by a second shielding, at one end of the reference conductor the first reference wire being connected to the second reference wire via a terminator,
a third shielding surrounding the signal and reference conductors,
wherein the signal and reference conductors have similar electrical and geometric properties,
wherein noise is induced in the signal and reference conductors by movement of the cable due to the tribo-electric effect such that the signal conductor carries the physiological signal and the noise and the reference conductor carries the noise; and
wherein the signal processor is configured to use the noise received on the reference conductor to extract the physiological signal from physiological signal and the noise carried on the signal conductor.

6. The signal measurement system as claimed in claim 1, wherein the signal measurement system further comprises a controller for controlling a measurement of the raw signal based on the noise signal of the reference conductor.

7. A method for electrically conducting signals via a signal cable comprising a signal conductor and a reference conductor, the method comprising:
electrically conducting via the signal conductor a first signal comprising at least a raw signal;
inducing a noise signal on the signal conductor and the reference conductor such that the first signal includes the raw signal and the noise signal; and
extracting the raw signal from the first signal by subtracting the noise signal from the reference conductor from the first signal;
in response to the noise signal being within a predetermined range, initiating a measurement of the raw signal; and
in response to the noise signal reaching a predetermined threshold, stopping the measurement of the raw signal.

8. The method as claimed in claim 7, further comprising the step of controlling a measurement of the raw signal based on the noise signal.

9. The method as claimed in claim 8, wherein the step of controlling comprises a step of initiating the measurement of the raw signal in response to the detected noise signal being below a selected threshold.

10. The method as claimed in claim 8, wherein the step of controlling comprises, in response to the detected noise signal being above or equal to a selected threshold, shutting down an ongoing measurement of the raw signal.

11. A signal cable configured to electrically conduct signals, the signal cable comprising:
a signal conductor for electrically conducting a first signal comprising a raw signal;
a reference conductor;
a shielding surrounding the signal and reference conductor; conductors;
wherein a noise signal is induced in the signal and reference conductors by a movement of the signal cable or by electromagnetic interference; and
wherein the signal conductor comprises a first and a second signal wire surrounded by a first shielding and wherein the reference conductor comprises a first and a second reference wire surrounded by a second shielding and wherein at one end of the reference conductor the first reference wire is connected to the second reference wire via a terminator.

12. The signal cable as claimed in claim 11, wherein the electrical and geometrical properties of the reference conductor are similar to the electrical and geometrical properties of the signal conductor.

13. The signal cable as claimed in claim 11, wherein the reference conductor also conducts a control signal.

14. The medical measurement system as claimed in claim 5, wherein the signal processor is configured to subtract the noise induced on the reference conductor from the signal on the signal conductor to extract the physiological signal.

15. The signal measurement system as claimed in claim 1 further comprising:
a feedback loop connecting the signal detector and the signal processor.

16. The signal measurement system as claimed in claim 1 wherein the signal processor is configured to stop a measurement of the raw signal if the noise signal reaches a predetermined threshold.

17. The signal measurement system as claimed in claim 1 wherein the signal processor is configured to initiate a measurement of the raw signal if the noise signal is within a predetermined range.

18. The method as claimed in claim 7 further comprising:
electrically conducting a control signal via the reference conductor.

19. The signal cable as claimed in claim 11, wherein the terminator connects the first and second reference wires such that the first and second reference wires are of equal lengths.

20. The signal measurement system as claimed in claim 5 wherein the signal processor is configured to stop a measurement of the raw signal if the noise reaches a predetermined threshold.

* * * * *